United States Patent [19]

McMahon

[11] Patent Number: 4,891,462

[45] Date of Patent: Jan. 2, 1990

[54] CYCLIZATION-DEHYDROGENTATION OF 1-ETHYL-NAPHTHALENE OVER COPPER ALUMINUM BORATE

[75] Inventor: Patrick E. McMahon, Wheaton, Ill.

[73] Assignee: Amoco Corporation, Chicago, Ill.

[21] Appl. No.: 186,358

[22] Filed: Apr. 25, 1988

Related U.S. Application Data

[63] Continuation-in-part of Ser. No. 925,326, Nov. 30, 1986, Pat. No. 4,740,647.

[51] Int. Cl.$^4$ .............................................. C07C 12/00
[52] U.S. Cl. ..................................... 585/411; 585/444
[58] Field of Search ................................ 585/411, 444

[56] References Cited

U.S. PATENT DOCUMENTS 4,729,979 3/1988 Zletz .................................... 502/202
4,755,497 7/1988 De Simone et al. ................ 502/202

Primary Examiner—Curtis R. Davis
Attorney, Agent, or Firm—Matthew R. Hooper; William H. Magidson; Ralph C. Medhurst

[57] ABSTRACT

A copper aluminum borate catalyzed cyclization-dehydrogenation process useful for converting 1-ethylnaphthalene to mixtures of vinylnaphthalens, acenaphthene and acenaphthylene.

7 Claims, No Drawings

CYCLIZATION-DEHYDROGENTATION OF 1-ETHYL-NAPHTHALENE OVER COPPER ALUMINUM BORATE

CROSS REFERENCE TO RELATED APPLICATION

This application is a continuation-in-part of Ser. No. 925,326 filed Oct. 31, 1986 and patented Apr. 26, 1988 (U.S. Pat. No. 4,740,647).

FIELD OF THE INVENTION

The present invention relates generally to processes for cyclization and dehydrocyclization of aliphatic moieties to afford compounds having at least one more ring moiety than the starting compound. More particularly, the invention is directed to a process for converting 1-ethylnaphthalene to a mixture comprising vinylnaphthalenes, acenaphthene and acenaphthylene, over a catalyst comprising at least one member selected from the group consisting of copper aluminum borate and zero valent copper on a support comprising aluminum borate.

DISCUSSION OF BACKGROUND ART

Acenaphthylene, acenaphthene, and vinylnaphthalenes are valuable precursors for the formation of pitch-based carbon fibers. Their use can improve carbon fiber processing and properties. Acenaphthene and acenaphthylene are also suitable for oxidation to 1,8-naphthalene dicarboxylic acid which in turn can be used to make polyester products.

Hussman et al. U.S. Pat. No. 4,740,647, of which the present application is a continuation-in-part, discloses that 1-ethylnaphthalene can be converted to acenaphthene or acenaphthylene using copper aluminum borate catalyst.

Satek U.S. Pat. No. 4,590,324 discloses dehydrogenation of alkylaromatics containing at least two carbons in at least one alkyl group to alkenylaromatics using a catalyst comprising metallic copper on a support comprising aluminum borate, the patent does not disclose or suggest use of the catalyst for cyclization of alkyl side chains separated by the bridging carbon of a polynuclear aromatic compound, as described in the present invention, to afford compounds having at least one more ring than the starting compound.

McArthur U.S. Pat. No. 4,024,171 discloses the use of catalysts comprising an aluminum borate support post treated with copper. Among the reactions disclosed for this catalyst are dehydrocyclization reactions. However, McArthur does not disclose crystalline copper aluminum borate having the unique x-ray diffraction pattern which is characteristic of the catalyst used in the present invention.

SUMMARY OF THE INVENTION

In its broadest sense the invention is a cyclization-dehydrogenation process which comprises contacting a polynuclear fused ring aromatic compound, said compound having an ethyl group bonded to a ring carbon adjacent a bridging carbon, with a catalyst comprising at least one member selected from the group consisting of copper aluminum borate and zero valent copper on a support comprising aluminum borate. The invention preferably comprises contacting a feed comprising a polynuclear aromatic compound having a portion thereof corresponding to the formula:

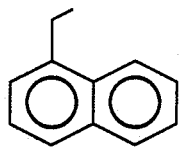

with a catalyst comprising at least one member selected from the group consisting of copper aluminum borate and zero valent copper on a support comprising aluminum borate, to obtain a reaction product comprising at least one member selected from the group consisting of compounds having portions corresponding to the following formulas:

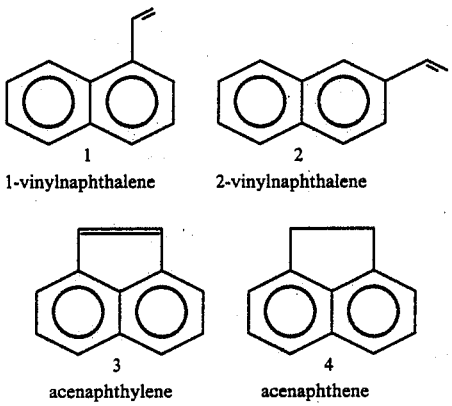

1-vinylnaphthalene    2-vinylnaphthalene acenaphthylene    acenaphthene

The terms "polynuclear aromatic compound" and "polynuclear fused ring aromatic compound" can include compounds having more than two fused aromatic rings, as well as compounds having incidental ring substitution which does not prevent the cyclization-dehydrogenation reaction of the present invention from occurring. Thus, for example, while 1-ethylnaphthalene can be used as the starting compound, the invention is not intended to exclude incidental substitution, for example alkyl substitution, at the 2 through 7 positions of the 1-ethylnaphthalene. Likewise, anthracenes or other higher polynuclear species are not excluded.

A preferred starting material is 1-ethylnaphthalene which can be converted to products 1 to 4, above or mixtures thereof.

When compared to commercially available catalysts, such as iron oxide, platinum on alumina, and platinum/rhenium on alumina, the copper aluminum borate catalyst used in the present invention results in much better conversion and selectivity to the cyclization and dehydrogenation products (1 to 4) depicted above with a concomitant reduction in unwanted cracking reactions. Naphthalene and 1-methylnaphthalene are the major by-products of such cracking. Preferably the copper aluminum borate catalyst is either co-synthesized or post-treated with an active metal. Preferred metals are potassium, nickel and palladium.

DETAILED DESCRIPTION

Copper aluminum borate and finely divided metallic copper on a support comprising aluminum borate are the subject of commonly assigned Zletz U.S. Pat. No.

4,729,979; of Zletz et al. U.S. Pat. No. 4,645,753; of Kouba et al. U.S. Pat. No. 4,613,707; and of Satek U.S. Pat. No. 4,590,324. These patents disclose the preparation, characterization and utility of copper aluminum borate and are hereby incorporated by reference.

As disclosed in Zletz U.S. Pat. No. 4,729,979, copper aluminum borate ($Cu_{2-X}Al_{6-y}B_4O_{17}M_mM'_nM''_y$ wherein M is a divalent metal, M' is a monovalent metal, m ranges from 0 to 0.8, n ranges from 0 to 1.6, X ranges from 0 to 0.8 and is equal to the sum of m+n/2, M'' is a trivalent metal and y ranges from 0 to 1.2) which is at least partially reducible with hydrogen under Temperature Programmed Reduction conditions at a temperature no more than 350° C., preferably having a surface area of at least 5 m² per gram and a pore volume of at least 0.04 cc per gram, is a new catalyst and further that copper aluminum borate can be treated with a reducing agent e.g. cumene to form a catalyst comprising finely divided metallic copper (zero valent copper) on a support comprising an aluminum borate. Part of the copper in the copper aluminum borate reacts with a reducing gas at relatively low temperature (about 175° to 350° C.) to form finely divided copper on the aluminum borate support.

When copper aluminum borate is used as a catalyst in the dehydrogenation of organic compounds or in a reaction medium containing a reducing gas, at least part of the copper in the copper aluminum borate is converted into finely divided copper on an aluminum borate support. In some reactions, such as in the dehydrogenation of alkylaromatics to alkenylaromatics, substantially all of the copper in the still active catalyst can be present as finely divided copper metal on an aluminum borate support, i.e., in the aluminum borate matrix. In other cases, the active catalyst always contains some copper aluminum borate. If part of the copper in copper aluminum borate is replaced with another divalent metal for example zinc, nickel or palladium, copper in the compound is still reducible to metallic copper at relatively low temperature.

While it is not clear at this point whether copper aluminum borate or copper on aluminum borate or combinations of the two is the true catalyst in dehydrogenation reactions and reactions employing a reducing gas, it has generally been found that the induction period for carrying out these reactions is reduced by treating the copper aluminum borate with a reducing agent such as cumene prior to the desired reaction to produce finely divided metallic copper on an aluminum borate support.

If neat copper aluminum borate having the empirical formula $Cu_2Al_6B_4O_{17}$ is viewed as having the structure $3Al_2O_3 \cdot 2CuO \cdot 2B_2O_3$, the reduction with CO or $H_2$ can be represented in its simplest terms as follows:

$3Al_2O_3 \cdot 2CuO \cdot 2B_2O_3 + 2H_2 \longrightarrow$ 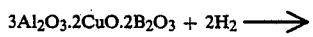

$3Al_2O_3 \cdot 2B_2O_3 + 2Cu + 2H_2O$ 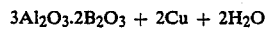

$3Al_2O_3 \cdot 2CuO \cdot 2B_2O_3 + 2CO \longrightarrow$ 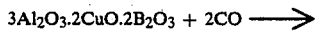

$3Al_2O_3 \cdot 2B_2O_3 + 2Cu + 2CO_2$ 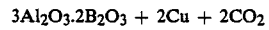

X-ray diffraction patterns of the products indicate that the aluminum borate crystal has the formula $2Al_2O_3 \cdot B_2O_3$ and that part of the $B_2O_3$ in the original copper aluminum borate crystal has been driven off and/or is present in the amorphous state. Partial replacement of the copper in copper aluminum borate with other divalent metals does not appear to interfere with the reduction of the copper to zero valent copper.

Unreduced copper aluminum borates (CuAB) have a distinguishing crystalline structure while substantially fully reduced CuAB (Cu on AB) has a different related crystalline structure as evidenced by the significant lines of their X-ray diffraction patterns. The 5.29 line has arbitrarily been set at 100 for Cu on AB in order to facilitate a comparison with ASTM data for such materials as CuAB and aluminum borate. The X-ray diffraction patterns in Table I show the significant lines for unreduced CuAB of this invention, substantially fully reduced CuAB (copper on aluminum borate) of this invention, $Al_4B_2O_9$ and copper.

X-ray data were determined by standard techniques. The radiation was the K-alpha double of copper, and a proportional counter spectrometer with a strip chart pen recorder was used. The peak heights, I, and the positions as a function of 2 times theta, where theta is the Bragg angle, were read from the spectrometer chart. From these the relative intensities, 100 $I/I_0$, where $I_0$ is the intensity of the strongest line or peak, and d (obs.), the interplanar spacing in A, corresponding to the recorded lines, were calculated. In Table I the relative intensities are given in terms of the symbols VVS=very very strong (over 100), VS=very strong (80-100), S= strong (50-80), M=Medium (20-50), W=weak (10-20) and VW=very weak (<10).

TABLE I

| dA | Cu on AB | CuAB | $Al_4B_2O_9$ | Cu |
|---|---|---|---|---|
| 7.50 ± .1 | | VW-M | | |
| 5.29 ± .05 | VS | VS | VS | |
| 5.00 ± .05 | | S | | |
| 4.92 ± .03 | W-M | | W | |
| 3.73 ± .03 | | W-M | | |
| 3.64 ± .03 | | VW-W | | |
| 3.58 ± .03 | VW-M | | VW | |
| 3.35 ± .03 | VW-M | W | M | |
| 2.98 ± .03 | | VW-W | | |
| 2.84 ± .03 | | VW-W | | |
| 2.78 ± .02 | VW | | | |
| 2.64 ± .02 | M | M-S | M | |
| 2.61 ± .02 | | W-M | | |
| 2.50 ± .02 | | W-M | | |
| 2.45 ± .02 | W-M | | W | |
| 2.26 ± .02 | | W-M | | |
| 2.22 ± .02 | W | | VW | |
| 2.16 ± .02 | | M | | |
| 2.13 ± .02 | M | | W-M | |
| 2.07 ± .02 | VVS | M | W | S |
| 1.97 ± .02 | VW-W | M | | |
| 1.91 ± .02 | VW | | VW | |
| 1.86 ± .01 | | W-M | | |
| 1.81 ± .01 | VVS | M | | M |
| 1.76 ± .01 | | VW | | |
| 1.67 ± .01 | W | W-M | | |
| 1.60 ± .01 | | W-VW | | |
| 1.555 ± .01 | W | W-VW | W | |

As indicated above, the substantially fully reduced copper aluminum borate X-ray diffraction lines correspond primarily to the X-ray diffraction lines of the $Al_4B_2O_9$ and copper.

The significant X-ray diffraction lines for copper aluminum borate are set forth below in Table A.

TABLE A

| dA | Strength |
|---|---|
| 5.29 ± .05 | VS |
| 5.00 ± .05 | S |
| 3.73 ± .03 | W-M |

TABLE A-continued

| dA | Strength |
|---|---|
| 2.64 ± .03 | M-S |
| 2.61 ± .02 | W-M |
| 2.50 ± .02 | W-M |
| 2.26 ± .02 | W-M |
| 2.16 ± .02 | M |
| 2.07 ± .02 | M |
| 1.97 ± .02 | M |
| 1.86 ± .01 | W-M |
| 1.81 ± .01 | M |

As disclosed in Satek, part of the copper salts or aluminum component can be replaced with divalent and/or trivalent metal salts such as nickel acetate, copper acetate, cobalt acetate, zinc acetate, magnesium nitrate, chromic acetate, ferrous or ferric acetate, etc. Divalent metal ions can appear in the copper aluminum borate as M in the above formula. X-ray diffraction data indicates that zinc, cobalt, nickel and magnesium have been successfully incorporated into copper aluminum borate crystals and, accordingly, X in the above formula can range from about 0.01 to 0.8, preferably about 0.05 to 0.5. Trivalent metal ions can appears as M" in the above formula, e.g., $Fe^{+++}$. However, chromium forms a chromite and appears to not to replace aluminum.

If desired, non-volatile cations such as alkali metal (M' in the above formula) or alkaline earth metal cations can be present during the preparation of the copper aluminum borate, however it is preferred in the present invention to introduce $K_2O$ by post-treating the calcined copper aluminum borate with $KHCO_3$ or $K_2CO_3$ solution using the incipient wetness technique.

For purposes of this invention the term "aluminum borate" is used in the generic sense to be inclusive of all aluminum borate compounds, such as pure or neat aluminum borate, copper aluminum borate, zinc aluminum borate, etc. "Copper aluminum borate" is used in the generic sense to be inclusive of all compounds containing divalent copper, trivalent aluminum and borate, comprising the X-ray diffraction pattern of $Cu_2Al_6B_4O_{17}$, such as pure or neat copper aluminum borate, copper zinc aluminum borate, aluminum borate/copper aluminum borate, copper aluminum borate/copper chromite, copper aluminum borate/alumina, copper-nickel aluminum borate, copper-palladium aluminum borate, copper-potassium aluminum borate, etc.

Briefly, the copper aluminum borate catalyst or zero valent copper on a support comprising aluminum borate for use in the cyclization-dehydrogenation process of the present invention can be prepared either from a gelled precursor in a liquid medium as disclosed in commonly assigned Zletz U.S. Pat. No. 4,729,979, incorporated herein by reference, or from a dry-mixed precursor as disclosed in commonly assigned U.S. Ser. No. 924,064, incorporated by reference. Regardless of which technique is used, preparation of the catalyst generally involves a three-step procedure comprising: (1) combining a source of divalent copper, trivalent aluminum and boron in the form of the oxide or borate, (2) drying the composition where necessary to remove water or diluent and (3) calcining the composition at a temperature sufficiently high to form crystalline copper aluminum borate having an X-ray diffraction pattern for $Cu_2Al_6B_4O_{17}$ as set forth in Table A.

In either the dry or liquid preparation of copper aluminum borate, suitable sources of copper include copper nitrate, copper acetate, copper carbonate, copper borate, basic copper carbonate ($CuCO_2.Cu(OH)_2$), copper acetate monohydrate, copper oxides and copper metal. Copper acetate monohydrate is preferred in the dry preparation. Suitable sources of boron include any solid boron containing reagent. Examples are boric acid, copper borate, aluminum borate, boron oxides, ammonium borate, ammonium hydrogen tetraborate, etc. Suitable sources of aluminum are alumina sols, aluminum nitrate, alumina, aluminum acetate, aluminum borate, etc. These components can be combined in approximately stoichiometric proportions to provide copper aluminum borate having the empirical formula $Cu_2Al_6B_4O_{17}$.

The preparation of copper aluminum borate for use in the present invention can be carried out by the liquid or gel technique described in the Zletz '979 patent. Using this technique, it is generally desirable to combine divalent copper, boron in the form of the oxide or borate ion, and trivalent aluminum in the form of aluminum salts or alumina in an aqueous medium. In order to avoid the introduction of any extraneous ions in the crystalline copper aluminum borate, it is generally desirable to avoid the presence of cations or anions that are not destroyed and/or volatilized during the subsequent drying and/or calcination step. The presence of volatile components in preparation of copper aluminum borate, such as water, $NH_3$, acetate ion, nitrate ion, etc., is advantageous in providing the copper aluminum borate with relatively high surface area and porosity desirable for most catalytic reactions. It is generally preferred to include ammonium salts or ammonium hydroxide in the above aqueous preparation to achieve the desired high surface area and porosity in the final catalyst.

Alternatively, copper aluminum borate catalyst useful in the present invention can be conveniently prepared using a solid-state method as disclosed in De Simone et al. commonly assigned co-pending U.S. Ser. No. 924,064, incorporated herein by reference. The solid-state preparation obviates the time-consuming and economically costly step of drying the catalyst precursor prior to calcining.

Briefly, the solid-state preparation of copper aluminum borate comprises (1) dry-mixing powdered reagents comprising suitable precursors of copper oxide (CuO), aluminum oxide ($Al_2O_3$), and boron oxide ($B_2O_3$) with at least about 3 wt % on a dry solids basis of a suitable solid binder to form a superficially dry copper aluminum borate precursor; (2) compacting the dry pre-cursor; and (3) calcining the precursor at a sufficiently high temperature to form crystalline copper aluminum borate. The terms "dry," "dry-mixed," "solid state," "solid," and "superficially dry" are intended to denote conditions, processes, or reagents which are essentially free of liquid materials. These terms are not intended to exclude the presence of ambient atmospheric moisture or the water of hydration in solid reagents. The terms "pre-cursor," "copper aluminum borate precursor," "dry-mixed precursor," etc., denote compositions which, upon calcination at a sufficiently high temperature, result in crystalline copper aluminum borate.

In the dry preparation, the solid reagents comprising suitable precursors of copper aluminum borate should be ground to a powder, individually or as a combination, through a 0.25 mm screen in a high speed grinder. It is important that similar particle sizes of all reagents be attained in order that the solid state reaction to form crystalline copper aluminum borate proceeds as uniformly as possible upon calcination. Following grinding, a superficially dry mixture is prepared by combining the powdered dry reagents with about 3-20 wt % of a suitable solid binder.

A suitable solid binder is one which is capable of holding the powdered reagents together following compaction in a pellet press or extrusion apparatus, and which will burn away upon calcination, thus imparting porosity to the pellet. Preferred binders are solid stearins and the like, graphite, or mixtures thereof. Sterotex, a commercially available vegetable stearin, is particularly well suited as it burns off at a lower temperature than graphite and results in a better catalyst. The preferred amount of binder is at least about 3% by weight of the powdered reagents on a dry solids basis, but up to about 20% may be employed. About 5 wt. percent of the binder is recommended. The binder material can be combined with the powdered reagents using a conventional mixing apparatus for a period of about 10 to about 60 minutes. After the above-prescribed mixing of the powdered reagents and solid binder is completed, the resulting superficially dry mixture can be either extruded or pelletized using conventional techniques and apparatus.

In either the liquid or solid state preparation part of the copper salts or aluminum component can be replaced with divalent and/or trivalent metal salts such as nickel acetate, copper acetate, cobalt acetate, zinc acetat, magnesium nitrate, chromic acetate, ferrous or ferric acetate, palladium nitrate, etc. Divalent metal ions can appear in the copper aluminum borate as M in the above formula. X-ray diffraction data indicates that zinc, cobalt, nickel, and magnesium have been substantially incorporated into copper aluminum borate crystals and accordingly X in the above formula can range from about 0.01 to 0.8, preferably about 0.05 to 0.50. Trivalent metal ions can appear as M" in the above formula, e.g., $Fe^{+++}$. However, chromium forms a chromite and appears not to replace aluminum. In addition, non-volatile cations such as alkali metal (M' in the above formula) or alkaline earth metal cations can be present during the preparation of the copper aluminum borate.

The catalyst precursor prepared by either of the methods described above should be calcined at a temperature in the range of from about 650° to about 1000°, preferably at least about 800° C. for about 1 to 24 hours, typically in air. The higher the calcination temperature, the shorter the calcination time. Calcinations below about 800° C. tend to provide a catalyst which has low activity for the reaction of the present invention. Other things being equal, the higher the calcination temperature the lower the surface area and porosity of the copper aluminum borate. Thus, at calcination temperatures exceeding 1000° C. the catalytic activity of the resultant material is substantially diminished. In the present invention the copper aluminum borate precursor mixture is initially calcined at a temperature of about 200° to 400° C., preferably about 300° C. for 3-4 hours to burn off volatiles, following which the temperature is increased to preferably between 780° and 860° C. for about 3-8 hours. The preferred calcining regime is 820° C. for about 4 to 8 hours.

Copper aluminum borate or copper on a support comprising aluminum borate can be treated with any of the metals or metal compounds conventionally used in catalysis. For example, copper aluminum borate can be treated or doped with an alkali metal or alkaline earth metal compound. Any one or more of the transition metals or compounds can be utilized such as the metals of Groups IB, IIB, IIIB, IVB, VB, VIB, VIIB and VIII of the Periodic Table. Suitable metals include zinc, cadmium, copper, silver, chromium, molybdenum, scandium, tungsten, manganese, titanium, rhenium, iron, cobalt, nickel, ruthenium, rhodium, palladium, osmium, iridium, vanadium, platinum, etc. These metals can be present in a concentration of from 0.01 to 30% by weight of the copper aluminum borate catalyst or copper on aluminum borate. These metals or metal compounds can be applied as salts, oxides, etc., and if desired, thermally decomposed to give the corresponding metal or oxides.

For the conversion of 1-ethylnaphthalene to 1-vinylnaphthalene, 2-vinylnaphthalene, acenaphthene and acenaphthylene, and mixtures thereof, the following modified copper aluminum borate catalysts have been found to be particularly well suited:

(1) Copper aluminum borate impregnated with 5 to 50 mole percent $K_2O$ using the incipient wetness technique;

(2) Copper aluminum borate co-synthesized with a palladium compound such that the calcined catalyst contains a mole percentage of palladium which is equal to about 0.05 to 10% of the sum of the mole percentages of copper and palladium in the catalyst.

(3) Copper aluminum borate co-synthesized with a nickel compound such that the calcined catalyst contains a mole percentage of nickel equal to about 1 to 20% of the sum of the mole percent copper and nickel in the catalyst.

The copper/co-metal catalysts (2) and (3) above can be represented by the following formulas:

(1) $Cu_{2-x}Pd_xAl_6B_4O_{17}$ (where x is about 0.001 to 0.2)
(2) $Cu_{2-x}Ni_xAl_6B_4O_{17}$ (where x is about 0.02 to 0.4)

The term "co-synthesis" or "co-synthesized" in connection with the copper palladium or copper nickel aluminum borate catalysts above means that the co-metal is introduced during preparation of the copper aluminum borate precursor as distinguished from post-treatment by doping or impregnating the calcined copper aluminum borate, the latter being preferred where the copper aluminum borate is to be modified with potassium.

EXAMPLE I

Copper aluminum borate was prepared as follows: 151.8 gm of copper acetate $(Cu(OAc)_2H_2O)$, 94.0 gm of boric acid $(H_3BO_3)$ and 166.2 gm of Davison VFA alumina (70% $Al_2O_3$; 30% $H_2O$) were hand-mixed in a jar for 1 min. and then ground thoroughly through a 0.25 mm screen in a high speed grinder to assure that all reagents were ground to a similar particle size for uniform mixing. The ground reagents were then dry-mixed with 5 wt. percent finely ground Sterotex. Roller mixing of the Sterotex and the ground reagents was carried out for about 30 minutes. The resulting liquid free precursor mixture was then formed into ⅛-inch diameter by 3/16-inch length pellets using a Stokes Model 521-2 four-ton single-punch powder compacting press. Crush strength of the pellets was maintained between 4.5 and 6.0 pounds. An Ametek Accuforce Cadet (40-pound) force gauge was used to monitor crush strength of the pellets. The pelletized precursor was then calcined using the following calcination program: (1) gradual increase from 150° C. to 300° C. at a rate of 75° C./hour requiring 2 hours; (2) 300° C. for 2 hours; (3) gradual increase from 300° C. to 820° C. at a rate of 130° C./hour requiring 4 hours; (4) 820° C. for 3 hours; and (5) gradually reduced from 820° C. to 150° C. over a period of about 10 hours.

EXAMPLE II

Copper aluminum borate as prepared in Example I was treated with 0.2% palladium as follows: 28 g of $Pd(NO_3)_2.H_2O$ was dissolved in 40 ml of de-ionized water. A syringe was used to evenly coat 62.2 g of copper aluminum borate pellets of Example I with the $Pd(NO_3)_2$ solution. The treated pellets were calcined as follows: (1) increase gradually from 120° C. to 300° C. over 2 hour period; (2) maintain at 300° C. for 3 hours; (3) gradually decrease from 300° C. to 120° C.

EXAMPLE III

Copper aluminum borate preparation was carried out in accordance with Examples I and II except that the copper aluminum borate was treated with 1.0 wt. % molybdenum (in the form of ammonium molybdate) instead of palladium.

EXAMPLE IV

Solid state preparation of copper aluminum borate incorporating molybdenum and palladium was carried out as follows: copper acetate, 36 g, boric acid, 22.3 g, Davison VFA alumina, 41.7 g, were mixed in a jar. Following mixing, ammonium molybdate, 1.8 g, and palladium (II) acetate, 0.42 g, were dry mixed with the copper aluminum borate precursor reagents. After all the reagents were mixed, the reagents were then ground for about 30 seconds through a 0.25 mm screen. To the milled mixture was added 5.11 g of Sterotex as binder followed by thorough dry-mixing of all the ingredients. The dry-mixed precursor mixture was then formed into pellets having a crush strength between 4.5 and 7.0 pounds. The pellets were calcined at 300° C. for about 3 to 4 hours and then at 820° C. for 8 hours.

EXAMPLE V

Copper aluminum borate doped with 10 mole % $K_2O$ was prepared as follows: 10.43 g of the copper aluminum borate catalyst pellets prepared in Example I was pre-reduced with cumene in the manner described in U.S. Pat. No. 4,729,979. To the reduced catalyst was added 5.2 ml of a 6% solution of $K_2CO_3$ in distilled $H_2O$ (0.312 g $K_2CO_3$) to coat the catalyst pellets. The pellets were then placed in an evaporating dish in a vacuum drying oven under nitrogen. The oven temperature was increased gradually from 40° C. to 100° C. over a period of several hours. The oven dried material (10.3 grams) was then placed in a furnace at 350° C. for four hours.

EXAMPLE VI

Example IV was repeated except the amount of $K_2O$ dopant was increased to 20 mole percent.

EXAMPLE VII

Example IV was repeated except that the amount of $K_2O$ dopant was increased to 30 mole percent.

EXAMPLE VIII

Example IV was repeated except that the amount of $K_2O$ dopant was increased to 40 mole percent.

EXAMPLE IX

Copper aluminum borate co-synthesized with nickel and having the formula $Cu_{1.8}Ni_{0.2}Al_6B_4O_{17}$ wherein the mole % nickel in the catalyst was 10% of the sum of the mole percentage of copper and nickel was prepared as follows: to a blender were charged (1) a nickelous nitrate 6.hydrate $(Ni(NO_3)_2.6H_2O)$ solution obtained by dissolving 4.85 g of the nitrate in 10 ml of deionized $H_2O$; (2) a cupric nitrate solution $(Cu(NO_3)_2.2\frac{1}{2} H_2O$, formula weight 232.59) was prepared by dissolving 34.89 g of the copper salt in 170 ml of deionized $H_2O$; (3) 326.92 gm PHF alumina-sol containing 7.8% $Al_2O_3$; and (4) a boric acid $(H_3BO_3)$ solution obtained by dissolving 20.61 gm of the boric acid (F.W=61.83) in 100 ml of deionized $H_2O$. After the above four components were added to the blender, the resulting mixture was first stirred with a spatula and then blended for 1 minute at low speed. The resulting sky blue foamy liquid had a pH of about 5.0. $NH_4(OH)$ was added to the mixture to cause gel formation. The addition of $NH_4(OH)$ was carried out by first blending $NH_4(OH)$ into the blended mixture with a spatula, followed by blending on low speed for 1 minute. Stiffening of the mixture occurred in the first 10 seconds, whereupon a spatula was used as needed to assist blending. The resulting mixture was deep blue with a pH of about 6.0. The material was distributed evenly in a thin layer on a plastic tray and allowed to air dry overnight. 101.53 g of the air dried material was oven dried at 120° C., 19" Hg for 20 hours with a nitrogen purge. When removed, the sample weight was 73.36 g indicating a 28.17 g weight loss. Into a calcining oven was placed 10.05 g of the oven dried material for calcining in air under the following regimen: (°C.)

| 120° | → | 165° | (1 hour) |
|---|---|---|---|
| 165° | → | 830° | (3 hours) |
| | 830° | | (8 hours) |
| 830° | → | 165° | (3 hours) |
| 165° | → | 120° | (1 hour) |
| 120° | → | 25° | (1 hour) |

Following calcination, the original 10.05 g sample was reduced to 5.89 g. To maximize the homogeneity of the catalyst composition, the calcined catalyst was reground and calcined again under the above temperature program. The recalcined catalyst afforded the following elemental analysis (wt. %) Cu 19%, Ni 2%, Al 27%, B 7% and O 45%. The catalyst had a BET surface area of 10 m²/g, a cumulative pore volume of 0.071 cc/g, and an average pore radius of 61 Å.

EXAMPLE X

Example IX was repeated except that the mole percent nickel present in the co-synthesis was increased to 15% of the total mole percent copper plus nickel to obtain a copper-nickel aluminum borate catalyst having the formula $Cu_{1.7}Ni_{0.3}Al_6B_4O_{17}$.

EXAMPLE XI

Example IX was repeated increasing the mole percent nickel to 20% of the total mole percent copper plus nickel to obtain a copper-nickel aluminum borate having the formula $Cu_{1.6}Ni_{0.4}Al_6B_4O_{17}$.

EXAMPLE XII

Copper aluminum borate co-synthesized with palladium and having the formula $CU_{1.998}Pd_{0.002}Al_6B_4O_{17}$ such that the mole % palladium in the catalyst is 0.1% of the sum of the mole percentage of copper and the mole percentage of palladium was prepared as follows: to a blender were charged (1) a copper nitrate solution obtained by dissolving 46.47 g of $Cu(NO_3)_2.2\frac{1}{2}$ $H_2O$ in 1970 ml deionized $H_2O$ (2) 392.31 g of alumina sol (7.8% $Al_2O_3$); and (3) a solution of boric acid obtained by dissolving 24.73 g of $H_3BO_3$ in 100 ml of deionized $H_2O$. The three components were first mixed with a spatula then blended for 1 minute on low speed resulting in a light blue foamy liquid. To the mixture was then added a palladium nitrate solution obtained by dissolving 0.042 g $Pd(NO_3)_2$ having a formula weight of 209.69 in 5 ml of deionized $H_2O$. All four components were then blended on low speed for 3 minutes. The pH of the solution was acidic. 10 ml of $NH_4(OH)$ was added resulting in a stiff mixture requiring hand mixing with a spatula in addition to low speed mixing with the blender. After mixing for several minutes the precursor was a bright blue and had the consistency of a gel. The gel was spread out to air dry in a thin layer overnight. After air drying, 127.82 grams of the sample were placed in a vacuum oven at 120° C., 20 in. hg for 17 hours. After oven drying the sample weighed 90.51 g. Into a calcining oven was placed 10.01 g of the oven dried material. The sample was calcined in the same manner as described in Example II. The calcined sample weighed 5.64 g. The sample was reground with a mortar and pestle and recalcined using the previously outlined regimen. The catalyst afforded the following analysis: Cu 21%, Pd 0.03%, Al 27%, B 7% and O, 45%. The catalyst had a BET surface area of 15 m²/g, a pore volume of 0.086 cc/g and an average pore radius of 79 Å.

EXAMPLE XIII

Example XII was repeated except that the mole percent palladium was increased to 5% of the sum of the mole percentage of copper and palladium to obtain a copper-palladium aluminum borate having the formula $Cu_{1.9}Pd_{0.1}Al_6B_4O_{17}$.

EXAMPLE XIV

Example XII was repeated except the amount of palladium was increased to obtain a copper aluminum borate of the formula $Cu_{1.8}Pd_{0.2}Al_6B_4O_{17}$.

EXAMPLE XV

Copper aluminum borate catalyst was prepared as follows: 100 g of boric acid was added to 960 ml of distilled $H_2O$ in a large beaker and dissolved by heating on a hot plate. In a separate beaker, 161.6 g of copper acetate $(Cu(OAC))_2 \cdot H_2O$ was added to 600 ml of moderately heated distilled $H_2O$. After the copper acetate was substantially dissolved (~15 min.), 120 ml of $NH_4OH$ was added to assist dissolution of the copper acetate. Separately, 1,588 g of PHF alumina sol ($Al_2O_3$) containing about 7.8% solids was poured into a large mixing apparatus, to which was added the hot boric acid solution followed by mixing at low speed with the top covered for about one minute. To the separate copper acetate solution was added an additional 120 ml of $NH_4OH$, at which point the copper salt was completely dissolved. The ammonia/copper acetate solution was then added gradually to the mixing apparatus containing the PHF alumina with mixing and stirring as needed. Throughout addition of the ammonia/copper acetate solution to the PHF alumina, hand stirring with a spatula was used to promote even formation of the gel which begins to form immediately upon addition of the copper solution to the alumina. Occasionally, the mixer was turned off in order that material collecting at the bottom of the mixer could be redistributed throughout the mixture. After all the copper solution was added, the gel was mixed at a moderate speed for about 5 minutes, until a smooth consistency was obtained. The gelled precursor was then spread out to dry for 1-2 days under a hood in a layer about 203 mm thick. The air dried catalyst was then collected in crystallizing dishes and placed in a vacuum oven overnight at a temperature of about 45° C. and with a nitrogen purge. Over a period of 2 additional days the vacuum oven temperature was raised gradually (10°-20° C.) until a temperature of 100°-100° C. was reached. The vacuum dried catalyst precursor was then transferred to alumina trays and calcined as follows: 120° C. to 300° C. gradually over 2 hours; 300° C. for 2 hours; 300° to 820° C. gradually over 3 hours; 820° C. for 3 hours; 820° to 120° C. gradually over 4 or more hours.

EXAMPLE XVI

This example illustrates the preparation of a copper aluminum borate/copper chromite catalyst. Into a blender was placed 300.77 g of an alumina sol (9.73 dry wt. % $Al_2O_3$, 0.2869 moles $Al_2O_3$) and 23.64 g boric acid (0.38 moles) dissolved in 250 ml of water. A copper nitrate/chromium acetate solution was prepared by dissolving 53.34 g copper nitrate (0.22 moles) in 60 ml water and adding thereto a solution of 15.56 g chromium acetate in 70 ml distilled water. On heating, the copper nitrate/chromium acetate solution became dark and opaque. The dark opaque solution was added to the blender and thoroughly mixed before transfer to petri dishes to dry. The petri dishes were placed in a vacuum oven and dried overnight at 55° C. at 20 inches (0.3 atm) vacuum. Over the next two days, the temperature was gradually raised to 106° C. while the vacuum pressure was increased to about 15 inches (0.5 atm), yielding 110.67 g of a dark blue solid. A portion of this material (27.09 g) was placed in a petri dish and calcined by heating as follows: 120° C. for 0.6 hr, 235° C. for 0.5 hr, 250° C. for 0.5 hrs, 375° C. for 0.8 hr, and then 400° C. After cooling for 1 hr the composition while still at 300° C. was placed in a desiccator overnight. The solid (13.76 g) was placed in a small alumina dish and calcined according to the following program: 40° C. for 2 hrs, 500° C. for 1 hr, 500° C. for 1.5 hrs, 735° C. for 3 hrs and then held at 750° C. and cooled. After cooling for 1.2 hrs, the temperature reached 482° C. and the dish was removed from the oven and placed in a desiccator, yielding 13.48 g of 11.2% copper chromite in copper aluminum borate.

EXAMPLE XVII

A hot solution of 21.63 g boric acid in 225 ml distilled water was added to 294.44 g of alumina sol (27.03 g alumina on a dry solids basis) in a blender while mixing. To this was added 31.43 g copper acetate and 4.35 g nickel acetate in 50 ml distilled water and 38 ml concentrated ammonium hydroxide. The solid salts remaining in the beaker were dissolved in 20 ml concentrated ammonium hydroxide and added to the blender. The beaker was then rinsed with distilled water and added to the blender. The stiff mixture was worked with a spatula and the blender action until a smooth gel was produced. The gel was transferred into plastic dishes for drying. After three days, the solids were transferred to two petri dishes and vacuum dried for 48 hours (0.25 atm, 50° C. initial temperature and 106° C. final temperature). Sixteen and seventeen hundredths g of the dry solids were calcined by heating from 115° C. to 260° C. for a 2 hr period, held at 260° C. for 1 hr, from 260° C. to 820° C. over a 3 hr period, held at 820° C. for 3 hrs and then cooled to 110° C. X-ray diffraction data indicated that the material was highly crystalline and had only a single component. The copper (90) nickel (10) aluminum borate had a surface area of 36 square meters per gram, 0.1289 ccs per gram pore volume and an average pore radius of 43 Å.

EXAMPLE XVIII

A hot solution of 23.05 g boric acid in 240 ml distilled water was added to 310.94 g alumina sol (28.52 g dry solids basis) in a blender while mixing. To this were added 40.54 g copper nitrate and 5.55 g zinc nitrate in 50 ml distilled water. Concentrated ammonium hydroxide (60 ccs) was then added and the mixture blended using a spatula until it was very smooth. The gel was placed on a tray and allowed to dry in air for 48 hrs and then dried under vacuum at 91° C. A portion of this solid was calcined at 380° C. to decompose nitrates and then at 825° C. for 3 hours. The copper (90) zinc (10) aluminum borate was highly crystalline and X-ray diffraction indicated that it was homogeneous. The material had a surface area of 35 square meters per gram, 0.1411 cc/g pore volume and an average pore radius of 59 Å.

EXAMPLE XIX

This example illustrates the preparation of a large batch of copper aluminum borate. The copper aluminum borate was prepared by (1) adding 400 g $H_3BO_3$ to 3384 ml distilled water and heating to dissolve;

(2) adding 646.4 g $Cu(OAc)_2.H_2O$ to 2400 ml water. Heating and stirring to substantially dissolve. After 15 minutes of heating adding one-half (480 ml) 29% aqueous $NH_3$ to speed dissolution of salt;

(3) weighing 6352 g PHF alumina (7.8% solids) to mixer bowl;

(4) adding hot boric acid solution to the PHF alumina in a mixer. Mixing slowly for 1 minute;

(5) adding remaining 480 ml (295 aqueous ammonium hydroxide) ammonia to $Cu(OAc)_2$ solution.

(6) after all solids were dissolved adding the ammonical copper acetate solution to the slowly mixing liquid in the blender forming a gel. Increasing the mixing speed and thoroughly mixing the gel for —5 minutes;

(7) removing the smooth uniform consistency gel from the mixer, and spreading to dry on large plastic sheets in layer —⅛" thick, for two days;

(8) collecting the air-dried catalyst (now shriveled into random sized flakes), placing in crystallizing dishes and loading into a vacuum oven under 20" of house vacuum (maintained with $N_2$ bleed) at 45° C. overnight;

(9) raising the vacuum oven temperature 10°–20° C. at a time at intervals over a period of two additional days until 100°–110° C. is reached;

(10) transferring the vacuum dried catalyst to alumina trays, then placing in a calcining over at 120° C. Calcination was as follows:

| | |
|---|---|
| 120° C. → | 2 hrs |
| 300° C. | 2 hrs |
| 300° C. → | 3 hrs |
| 820° C. | 3 hrs |
| 820° C. → | >4 hrs |

In the following examples demonstrating cyclization-dehydrogenation according to the present invention, the reactions were carried out in a gas-phase flow-through fixed-bed reactor. Reactors were ¾ inch O.D. by 21 inch quartz tubes fitted with a ¼ inch thermowell; catalyst first was located approximately 1 inch below center. This allowed catalyst to be loaded in such a way as to minimize empty reactor space in the hottest reactor zones. Heat was provided by single zone Lindberg furnaces regulated by standard on-site controllers. Liquid reactants were fed and regulated by Harvard syringe pumps. Gaseous reactants were regulated with micrometering valves, measured by gas bubble meters. Liquid products were collected in a series of traps employing water/ice, dry ice/acetone, and a water-cooled spiral condenser; gaseous products were not collected.

Reactants and products were identified and quantified by GC analysis. Product identities were determined and confirmed by GC of authentic samples and GC/mass spectroscopy analysis along with GC-IR and NMR in some cases.

| Reaction Parameters | |
|---|---|
| Liquid Flow Rate | 2–10 ml solution/hour. Preferably 2.3 ml/hr of a 25% solution of 1-ethylnaphthalene in benzene. |
| WHSV | 0.05–0.4; preferably 0.1. |
| Diluent Ratio | 30–160 to 1 mole diluent per mole reactant, diluents include nitrogen, benzene, steam. |
| Temperature | 500° C.–800° C.; preferably 580° C.–700° C. |
| Catalyst Amount | 3 to 10 grams. |

Product concentrations reported have been calculated from area percent data.

EXAMPLE XX

Using the general reaction procedures summarized above, copper aluminum borate of Example I was loaded into a quartz reactor tube. The starting material 1-ethylnaphthalene was fed to the reactor at WHSV of 0.04. The diluent used was benzene at a diluent ratio of 80:1. The reaction was carried out at 640° C. After 30 hours on stream conversion was 91% and selectivity to the products 1-vinylnaphthalene, 2-vinylnaphthalene, acenaphthene and acenaphthylene was 92%. Product distribution of these products normalized to 100% was as follows:

| | |
|---|---|
| 1-vinylnaphthalene | 89% |
| 2-vinylnaphthalene | 2% |
| Acenaphthene | 3% |
| Acenaphthylene | 6% |

EXAMPLE XXI

Using the general reaction procedures outlined above, copper-palladium aluminum borate of Example XII was loaded into a quartz reactor tube. The reactant 1-ethylnaphthalene was fed to the reactor at WHSV of 0.1 using benzene diluent at a ratio of 80:1. The reaction was carried out at 640° C. Conversion was 78% and selectivity was 96%. Product distribution was as follows:

| | |
|---|---|
| 1-vinylnaphthalene | 67% |
| 2-vinylnaphthalene | 6% |
| Acenaphthene | 12% |
| Acenaphthylene | 15% |

EXAMPLE XXII

Example XXI was repeated except the reaction temperature was 670° C. After 30 hours conversion was 89% and selectivity to the four desired products was 42%. Product distribution was as follows:

| | |
|---|---|
| 1-vinylnaphthalene | 63% |
| 2-vinylnaphthalene | 3% |
| Acenaphthene | 14% |
| Acenaphthylene | 20% |

EXAMPLE XXIII

Example XX was repeated using copper-nickel aluminum borate of Example IX and a reaction temperature of 620° C. After 21 hours conversion was 79% and selectivity to the desired products was 89%. Product distribution was as follows:

| | |
|---|---|
| 1-vinylnaphthalene | 64% |
| 2-vinylnaphthalene | 5% |
| Acenaphthene | 10% |
| Acenaphthylene | 21% |

After 71 hours, conversion was 39% and selectivity was 80%. Product distribution had changed to:

| | |
|---|---|
| 1-vinylnaphthalene | 25% |
| 2-vinylnaphthalene | 0% |
| Acenaphthene | 32% |
| Acenaphthylene | 43% |

EXAMPLE XXIV

Example XXIII was repeated using a reaction temperature of 660° C. After 77 hours conversion was 78% selectivity 80%. Product distribution was:

| | |
|---|---|
| 1-vinylnaphthalene | 19% |
| 2-vinylnaphthalene | 3% |
| Acenaphthene | 45% |
| Acenaphthylene | 33% |

EXAMPLE XXV

Example I was repeated except the catalyst used was copper aluminum borate pre-reduced with cumene and then doped with 10 mole % $K_2O$ (Example V). Reaction temperature was 630° C. The results were as follows:

| | 30 Hrs on Stream | 90 Hrs | 140 Hrs |
|---|---|---|---|
| Conversion | 80 | 75 | 80 |
| Selectivity | 83 | 80 | 67 |
| 1-vinylnaphthalene | 69 | 52 | 38 |
| 2-vinylnaphthalene | 2 | 2 | 2 |
| Acenaphthene | 12 | 16 | 21 |
| Acenaphthylene | 17 | 30 | 39 |

What is claimed is:

1. A cyclization-dehydrogenation process which comprises contacting a polynuclear fused ring aromatic compound, said compound having an ethyl group bonded to a first ring carbon adjacent a bridging carbon, with a catalyst comprising at least one member selected from the group consisting of copper aluminum borate and zero valent copper on a support comprising aluminum borate which process effects cyclization across said bridging carbon, the cyclization taking place between (a) the ethyl carbon furthest from the ring and (b) a second ring carbon located two carbons from said first ring carbon and separated therefrom by said bridging carbon.

2. A cyclization-dehydrogenation process which comprises contacting a feedstock comprising a polynuclear aromatic starting compound having a portion thereof corresponding to the formula:

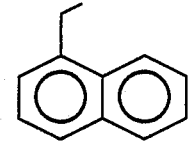

with a catalyst comprising at least one member selected from the group consisting of copper aluminum borate and zero valent copper on a support comprising aluminum borate, to obtain a reaction product comprising at least one member selected from the group consisting of compounds having portions which correspond to the formulas:

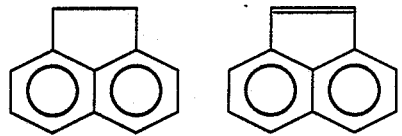

3. The process of claim 2 wherein the feedstock comprises 1-ethylnaphthalene and the reaction products comprise one or more of 1-vinylnaphthalene, 2-vinylnaphthalene, acenaphthene and acenaphthylene.

4. The process of claim 3 wherein the catalyst comprises copper aluminum borate having the formula $Cu_2Al_6B_4O_{17}$ and the x-ray diffraction lines of Table A.

5. The process of claim 3 wherein the catalyst comprises copper aluminum borate co-synthesized with palladium and having the formula $Cu_{2-x}Pd_xAl_6B_4O_7$ where x is about 0.001 to 0.2.

6. The process of claim 3 wherein the catalyst comprises copper aluminum borate co-synthesized with nickel and having the formula $Cu_{2-x}Ni_xAl_6B_4O_7$ where x is about 0.02 to 0.4.

7. The process of claim 3 wherein the catalyst comprises copper aluminum borate doped with about 5 to about 50 mole % $K_2O$.

* * * * *